United States Patent [19]

Dedden et al.

[11] Patent Number: 4,665,036
[45] Date of Patent: May 12, 1987

[54] ILLUMINATING DEVICE FOR THE OPTICAL, PARTICULARLY IMAGE-ANALYTICAL EVALUATION OF MICROBIOLOGICAL OBJECTS

[75] Inventors: Hubert Dedden, Langenfeld; Dietrich Förster, Hilden; Horst Rost, Moers; Alfred Zembrod, Bergisch-Gladbach, all of Fed. Rep. of Germany

[73] Assignee: Bayer Aktiengesellschaft, Leverkusen, Fed. Rep. of Germany

[21] Appl. No.: 734,921

[22] Filed: May 16, 1985

[30] Foreign Application Priority Data

Jun. 4, 1984 [DE] Fed. Rep. of Germany ....... 3420760

[51] Int. Cl.$^4$ .............................................. C12M 1/20
[52] U.S. Cl. ..................... 435/301; 350/525; 435/808
[58] Field of Search .......... 435/287, 297–301, 435/DIG. 808; 350/319, 525; 356/244

[56] References Cited

U.S. PATENT DOCUMENTS 4,221,867 9/1980 McFadden .................. 435/808
4,407,569 10/1983 Piller et al. ..................... 350/525

FOREIGN PATENT DOCUMENTS 1162367 8/1969 United Kingdom ................ 350/525

Primary Examiner—Samuel Scott
Assistant Examiner—Noah Kamen
Attorney, Agent, or Firm—Sprung Horn Kramer & Woods

[57] ABSTRACT

An illuminating device with a diffused, radiating, surface light source (3) and an aperture system positioned between the light source and the object is provided. The aperture system is formed by two optically complementary aperture screens (4, 5) which are disposed in series, and are spaced apart. The first aperture screen (4) thereby consists of a large number of transparent circular discs (8), positioned at intervals on an opaque base, and a second aperture screen (5) consists of a large number of opaque circular discs (9), positioned at intervals on a transparent base. The diameter of the opaque circular discs (9) is larger than that of the transparent circular discs (8), so that the circular discs of the two aperture screens (4, 5) overlap in the projection. The microbiological structures used generally have a large number of almost circular areas which are positioned in a regular surface pattern on a transparent base or round one or some relatively large circular transparent areas on a light-dispersing base. With the illuminating device according to the principle of the complementary aperture screens, the contrast of such microbiological structures in relation to the base could be substantially improved.

8 Claims, 7 Drawing Figures

ILLUMINATING DEVICE FOR THE OPTICAL, PARTICULARLY IMAGE-ANALYTICAL EVALUATION OF MICROBIOLOGICAL OBJECTS

BACKGROUND OF THE INVENTION

This invention relates to an illuminating device for the optical, particularly image-analytical evaluation of a microbiological structure. The illuminating device comprises a diffused, radiating, surface light source and an aperture system positioned between the microbiological structure and the light source. Instruments for examining bacterial growth on suitable nutrient media are today an indispensable aid to microbiological research. The nutrient media are thereby injected either at predetermined positions or distributed over the entire surface. Characteristic patterns of growth then arise, (hereafter described as microbiological structure), which either have a periodical or a surface object structure. The character, that is the macroscopic appearance and the optical properties important for an image-analytical evaluation of the microbiological structure (absorption, refraction, diffusion) depend on which process is used for examining the bacterial growth. The following microbiological standard processes have become established:

1. agar dilution (AD)
2. microdilution (MD)
3. inhibition zone measurement on petri dishes (IZ-P)
4. inhibition zone measurement on large rectangular plates (IZ-XY)
5. colony counting (CC).

These processes are described in detail in the technical literature and thus do not need to be described in more detail here. In common with all processes, the image-analytical problem, object positions or surface areas, in which bacterial growth arises, can be localized by scanning with a video camera and/or by quantitative evaluation. The extent to which bacterial growth arises depends on the effect of particular antibiotic quantities, which are incorporated into the nutrient media. When using the agar- and microdilution process, bacterial growth can only arise at determined positions. On the other hand, a variable surface bacterial growth takes place in the case of the inhibition zone measurement method. In the colony counting method, a pointwise bacterial growth occurs in the form of individual colonies with a diameter up to a few millimeters. The positions of the individual colonies are, however, distributed over the nutrient medium surface in an irregular manner.

The image-analytical evaluation of microbiological structures is frequently connected with problems, since the structures are often of very low-contrast and are embedded in an uneven ("irregular") environment, the brightness distribution of which substantially corresponds with the brightness distribution of the structure. In such cases, further improvements can hardly be achieved even by using electronic means. On the other hand, it has been shown that the contrast between objects and background substantially depends on the type of illumination. In the initial phase of the microbiological examination methods, optical transmission measurements were additionally carried out. Modern apparatus for examining biological samples generally operates by this illumination principle. After experimental indications had been obtained, such that the contrast ratios were allowed to increase, in all respects, by an improved illuminating device, further developments were carried out in this area and finally a new illuminating device was designed. Thus the problem was that the used stationary television camera scans all microbiological structures used from above by a light scattering system, evaluates them imagewise and the microbiological structures are illuminated from below by oblique incident light, such that direct linear incident light is avoided in the camera. The camera should thus only detect light which is scattered from within the microbiological structure, while the direct rays emitted from the light source are cut out. This principle should be realised on any substrate material for all growth patterns and plate sizes (square plates up to 30 cm×30 cm in size).

SUMMARY OF THE INVENTION

This task is achieved according to the invention in that, starting from an illumination device with a diffusely radiating plane light source and an aperture system positioned between the microbiological structure and the light source, (a) the aperture system is formed by two optically complimentary aperture screens disposed in series and with a spacing between them,
(b) the first aperture screen consists of a large number of transparent, circular discs positioned at intervals on an opaque background, and the second aperture screen consists of a large number of opaque circular discs positioned at intervals on a transparent background,
(c) and the opaque circular discs are larger in diameter than the transparent circular discs, so that the circular discs of the two aperture screens overlap in the projection.

An illuminating device designed according to this principle in all microbiological measuring processes resulted in an increase in contrast ratios and thus increased reliability, reproducibility and precision of the image-analytical evaluation.

If the microbiological structure consists of a large number of individual objects, as is the case, for example, with the agar- and microdilution process, further improvement can be achieved by the following constructive measures: the two aperture screens are positioned in tandem and below the microbiological structure in such a manner that the central points of the circular discs of the two aperture screens lie on the extended connecting straight lines from a vanishing point on the optical axis to the object position. The vanishing point generally corresponds to the central point of the camera lens. With this arrangement, an optimum cutting out of direct light-incidence in the camera can be achieved, if the aforementioned condition applies for all perspective angles, at which the camera observes the object positions.

In contrast to the agar dilution- and microdilution process, the microbiological structure to be examined consists, in the inhibition zone measurement, of relatively large surface objects. In this case, the two aperture screens are advantageously disposed in series, such that the transparent circular discs of the first aperture screen are positioned substantially concentrically in a parallel projection to the opaque circular discs of the second aperture screen.

The following ranges were determined for the optimum geometry of the aperture screens:

(a) the spacing h between the two aperture screens is selected such that it is from 0.5 to 5 times larger than the diameter of the transparent circular discs of the first aperture screen.

(b) The difference $d_2-d_1$ in diameter of the two circular discs of both aperture screens is selected within a range which is from 5 to 100% of the spacing of the two aperture screens.

Suitable photographically produced masks based on commercial photographic material are used as aperture screens. Such masks can be easily produced and have the advantage, moreover, that they are of very small thickness and thus light reflections on the inner edge of the transparent circular discs are substantially avoided.

In the microdilution process, the biological samples are in a matrix-like arrangement of cup-like wells (microtitre plates). The first aperture screen is now advantageously directly integrated into the sample holding device; that is, the first aperture screen is, in this case, part of the sample holding device used for the microbiological structure. In the case of the illuminating device used for the microdilution process, the illuminating device used has, moreover, proved worthwhile, if a further aperture screen with transparent circular discs is positioned above the sample holding device, that is between the sample holding device and the video camera. Scattered light can thus be cut out, which arises in the sample holding device, for example, at the edges of the cup-like wells by dispersion or reflection.

The following advantages are achieved with the invention:

1. In contrast to the conventional illuminating devices, the contrast of the microbiological structure in relation to the base could be substantially improved. In the case of the microbiological structures used here, a large number of almost circular patches generally arise, which are positioned in irregular surface patterns on a transparent background (agar dilution) or, respectively, a few relatively large circular transparent areas on a light-scattering background (inhibition zone measurement). It is in the nature of these structures, that the patches are optically only slightly distinguished from their background, owing to the low contrast ratio, that is, they have only relatively faintly distinct contours. The contrasts are substantially increased by the new illuminating device, such that the image-analytical evaluation is substantially facilitated and in many cases is made possible for the first time. The image-analytical evaluation comprises the recognition of the objects, the position thereof and the geometric and optical measurement thereof.

2. The constructive basic principle of the illuminating device is the same for all microbiological examination methods, so that apart from additional devices which are easy to apply, the same apparatus is always used and no costly reconstruction is required.

3. An important constructive advantage lies in the fact that the illuminating device can be designed to save space, since the aperture system and the light source can be positioned at a small spacing in tandem and thus only a small overall height is necessary. Subsequent installation in already existing apparatus is thus above all facilitated.

4. In using photographic shadow mask technology, the aperture screens can be produced with the desired precision also at a favourable cost.

Embodiments of the invention are explained in more detail below by means of drawings:

DETAILED DESCRIPTION OF THE PREFERRED EMBODIMENTS

Figure 1:
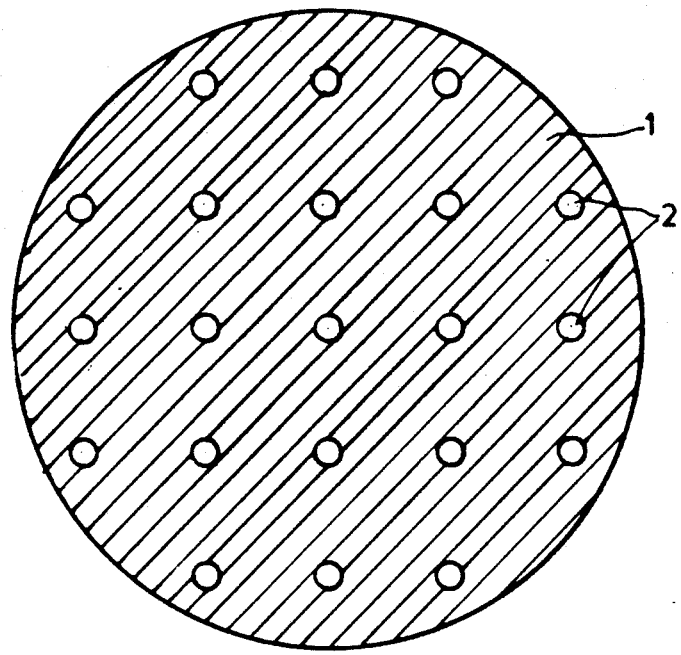
FIG. 1 shows a top view of the sample holding device used for the agar dilution process.
Figure 2:
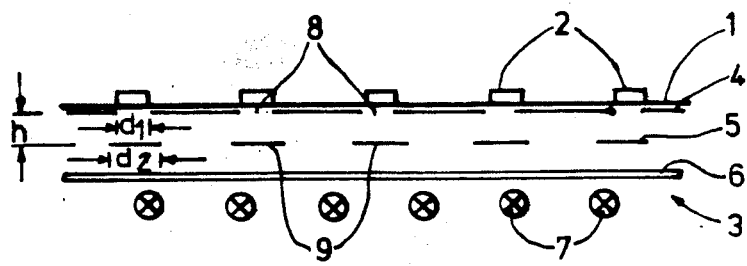
FIG. 2 shows the important elements of the illuminating device in the agar dilution process (side view)

According to FIG. 1, 21 inocculation positions are applied for the agar dilution process in a regular lattice-type pattern, on a nutrient medium 1, in a petri dish. Bacterial growth can take place at these 21 positions. A circular ring then arises around the inocculation positions. Since the type of bacteria generally vary from position to position, and the growth of all bacteria is influenced by a uniform antibiotic concentration incorporated into the nutrient medium, bacterial growth is to be observed at some inocculation positions, while at other positions no growth occurs. The plate with the nutrient medium is transparent and is illuminated from below by indirect light. The illuminating device used for this purpose is shown in FIG. 2.

It consists of a diffusely radiating plane light source 3 and an aperture system positioned above it with a first aperture screen 4 and a second aperture screen 5. The diffusely radiating plane light source 3 consists of a light-diffusing screen 6, which is illuminated from below by a large number of lamps 7. The lamps 7 are on a plane surface and are positioned at the same spacing from each other in the X- and Y-directions. The first aperture screen 4 consists of a large number of transparent circular discs 8 on an absorbent (opaque) background and the second aperture screen 5 consists of a large number of absorbent (opaque) circular discs 9 on a transparent base. The two aperture screens 4 and 5 are thus optically complementary. The second aperture screen 5 is again shown more clearly in FIG. 3. The black circular discs 9 on the transparent base 10 can be seen, which are positioned at a regular spacing in two directions vertical to each other. On the complementary first screen 4, the circular discs 8 are transparent, while the base is black. The first screen thus shows, apart from the characteristic geometric data, a photographic negative of the second aperture screen. The diameter $d_2$ of the opaque circular discs 9 is somewhat larger than the diameter $d_1$ of the transparent circular discs 8. Moreover, the two aperture screens are positioned relative to each other, such that the opaque circular discs 9 of the second aperture screen are concentric to the transparent circular discs 8 of the first aperture screen. It can be seen from FIG. 2, that the circular discs of the two aperture screens overlap in the parallel projection. The transparent circular discs 8 of the first aperture screen 4 are assigned as concentric circular screens to the inocculation positions 2 on the nutrient medium 1. The inocculation positions 2 are here equal to the object positions of the microbiologcial structure.

The spacing h of the two aperture screens 4 and 5 is selected such that a substantially positionindependent constant luminous intensity prevails in the object plane. Empirically this condition can be easily found, in that a diffusing screen is brought, in place of the sample holding device, within the object plane, which is positioned tightly above the aperture screen 4.

Regarding the dimensions of the aperture screens (geometrical characteristic values) the following conditions apply in practice:

$$0.2h \leq d_1 \leq d_2 \leq 2h \text{ and } 0.05h \leq d_2 - d_1 \leq h$$

The production of the aperture screens 4 and 5 takes place in a simple manner by illuminating photographic film material, which is covered by a shadow mask. The aperture screen complementary thereto is obtained when a photographic negative of the first film mask is completed. The photographically produced aperture screens have the advantage that they have only a small thickness in relation to apertures consisting of metal.

The mode of operation of the illuminating device according to FIG. 2 is based on the fact that all object positions 2 are illuminated diagonally from below indirect illumination) and are directly cut off by the rays emitted straight from the diffused light source 3 in the direction of the television camera used for imaging and evaluating the microbiological structure. For illuminating the inocculation positions 2, only those quantities of light contribute, which are admitted by the transparent areas in the two aperture screens 4 and 5. With the optical axis as a reference line, these are only the diagonally-incident light quantities from all angles of the diffused illumination. Diagonal illumination is thus achieved for all possible growth positions on the nutrient medium. Moreover, each inocculation position is evenly illuminated on the nutrient base from all sides with diagonally-incident light, owing to the concentric positioning of the transparent circular disc belonging to the aperture screen 4 and the corresponding concentrically optical opaque circular disc of the aperture screen 5. The whole illumination device, which consists of the aperture screens 4 and 5 as well as the diffused planar light source 3, can be produced with an overall height of a few centimeters (from 5 to 10 cm) to save space.

Figure 4:
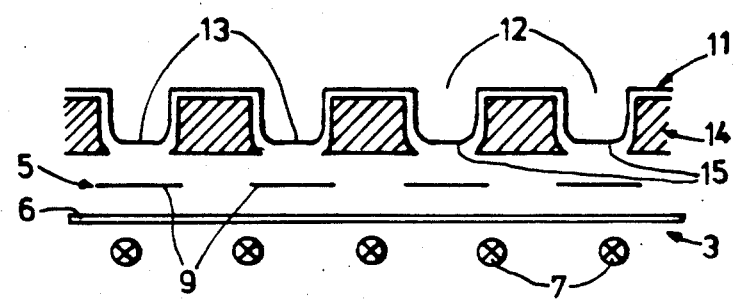
FIG. 4 shows the important elements of the illuminating device in the microdilution process (side view)

In the microdilution process, so-called microdilution plates 11 are used (see FIG. 4). They consist of a matrix arrangement of usually 8×12 cup-like wells 12 and are produced from a transparent plastics material. The bottom part 13 of the wells 12 is shaped either semi-spherical or flat or in other ways. Substances of different antibiotics are filled into the wells 12 in varying quantities. Along a row (an eight well row or a twelve well row), the same antibiotic is fed in in increasing quantity. Bacteria are then added to a nutrient liquid. The microdilution plate 11 is then incubated at 37° C., whereby bacterial growth can take place. In those wells 12, in which growth is taking place, optical turbidity is also developing.

The microdilution plate 11 is inserted in a holding device 14 consisting of metal. The holding device 14 contains bore-holes, into which the cup-like wells 13 of the microdilution plate 11 fit. The inserted microdilution plate 11 is thereby clearly mechanically fixed. On the bottom of the holding device 14, circular orifices 15 are positioned, which expose the bottom area of the cup-like wells 13 for light incident from below. The orifices 15 in the holding device 14 correspond in their effect to the transparent circular discs 8 of the first aperture screen 4 in FIG. 2. The first aperture screen is thus integrated into the holding device 14. The microbiological structure to be examined is thus formed by the total number of objects (nutrient solutions with bacteria) in the wells 13.

Figure 3:
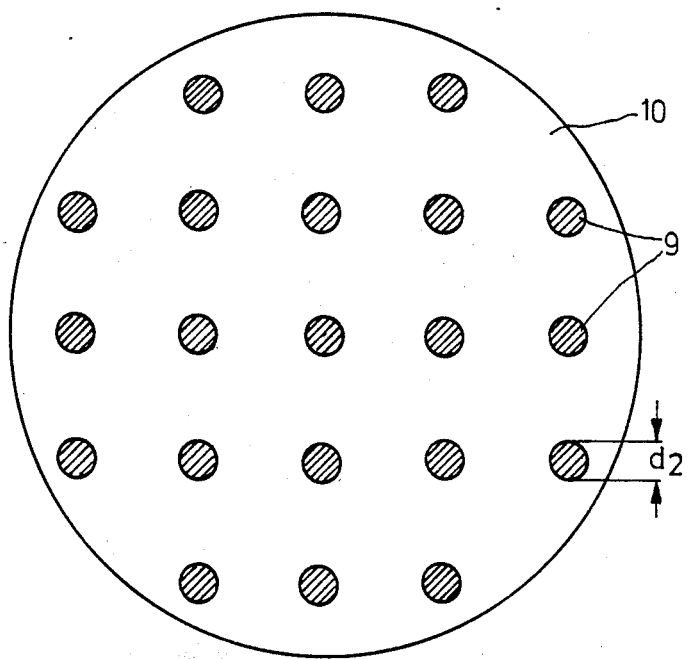
FIG. 3 shows the top view of an aperture screen.

Furthermore, the illuminating device is constructed in a similar manner to that in the agar dilution process according to FIGS. 1 to 3. The second aperture screen 5 again consists of black circular discs 9 with a somewhat larger diameter than the circular orifices 15 and is positioned at a short spacing (a few millimeters up to centimeters) such that the black circular discs 9 lie concentrically to the orifices 15. A diffusing screen 6 again acts as planar light source, which screen is illuminated from below by a large number of lamps 7. The first aperture screen formed by the orifices 15 and the second aperture screen 5 complementary thereto, prevent direct light-incidence on the wells 13 as in the arrangement according to FIG. 2. The samples in the wells 13 are thus only hit by light rays which are emitted from the light source 3 at an oblique angle. If the microdilution plate 11 is observed from above, the wells with bacterial growth optically intensively stand out owing to the scattering of light produced by the turbidic medium. the scattering of light is quantitatively evaluated by means of a video camera.

Figure 5:
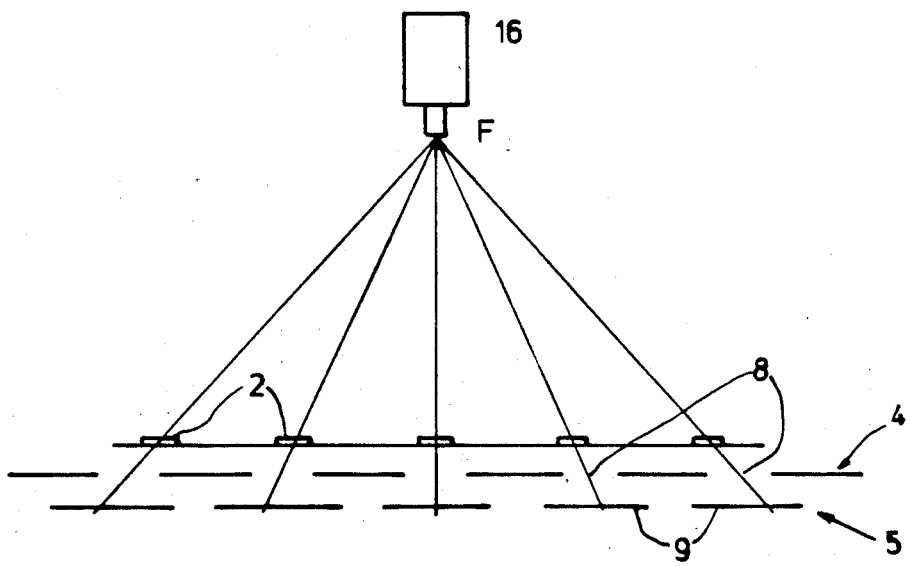
FIG. 5 shows an embodiment of the illuminating device for the agar dilution process.
Figure 6:
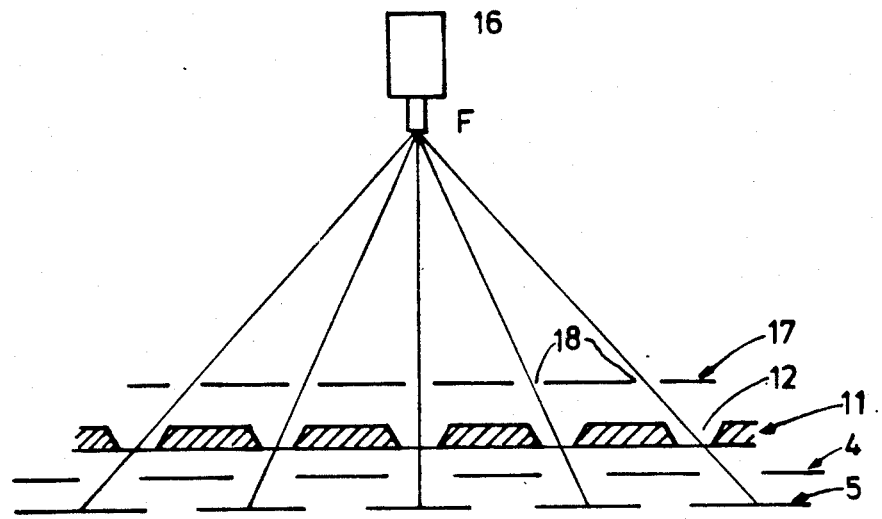
FIG. 6 shows an embodiment of the illuminating device in the microdilution process.

An alternative arrangement of the aperture system with an improved diagonal light effect is described by means of FIGS. 5 and 6. FIG. 5 thereby corresponds to the agar dilution process and FIG. 6 to the microdilution process. The improvement lies in the fact that the transparent circular discs 8 of the first aperture screen 4 and the abosrbent circular discs 9 of the second aperture screen 5 are not positioned concentrically to each other, but are moved against each other from the side. The positioning is such that the central points of the circular discs of the two aperture screens lie on the extension of the connecting straight lines of a vanishing point F, on the optical axis, to the object positions (injection positions). The diameter of the transparent discs 8, as in the arrangement according to FIG. 2 to 4, is again smaller than the diameter of the opaque discs 9 in the aperture screen 5. In so far as the afore-mentioned condition is adhered to for all perspective angles, under which the camera 16 observes the innocculation positions 2, an optimum diagonal light illumination is guaranteed, since the diameter of the opaque discs 9 in the aperture screen 5 only needs to be slightly larger than the diameter of the transparent discs 8.

In the production of aperture screens, this perspective illumination effect has to be taken into account. This takes place in a simple manner, in the aforementioned photographic production, by means of shadow masks, by using a light source which is as point-like as possible and the spacing between the light source and the photographic films is selected such that it corresponds to the spacing of the front lens of the front lens of the camera objective from the aperture screens 4 and 5 in the apparatus according to FIG. 5 (or FIG. 6) and during illumination the spacing of the films has the same spacing as during the use thereof in the illuminating device.

According to FIG. 6, the perspective illumination effect is used in the microdilution process. The arrangement of the aperture screens 4 and 5 corresponds to the arrangement in FIG. 5. The object positions 2 correspond to the solutions in the cup-like wells 12 in the sample holding device 11. In order to cut out stray light, which is produced by scattering or reflection in the sample holding device 11, a further aperture screen 17 with transparent circular discs 18 is positioned above the sample holding device 11. Likewise, the central points of the circular discs 18 lie on the connecting straight lines between the central point of the front lens of the video camera 16 and the object positions.

Figure 7:
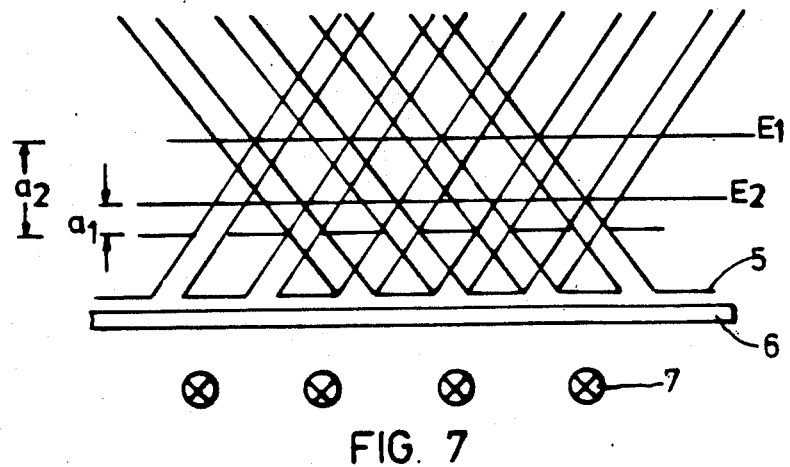
FIG. 7 shows the important elements of the illuminating device used for the inhibition zone measurement and colony counting (side view).

By means of FIG. 7, the arrangement for the production of an indirect illumination is described for surface bacterial growth patterns. The arrangement is particularly suitable for the inhibition zone measurement on round petri dishes, the inhibition zone measurement on large square plates by means of a two-dimensional scanning table and the colony counting. In the inhibition zone measurement, the diameters of generally circular inhibition zones must be determined. For this purpose, the surfaces must be image-analytically evaluated in the region of an inhibition zone.

In the colony counting, after inocculating a diluted bacterial suspension and incubation at 30° C., colonies result in each case from individual bacteria, of which the position and quantity within the plane are not known. The object is now to determine the quantity of colonies. For this reason, the whole surface or a representative section of the surface must also be image-analytically scanned here.

The principle of the complementary aperture screens is again used for illuminating these microbiological structures. The arrangement is modified in relation to the embodiments according to FIGS. 1 to 6. In the above described methods, the aperture spacing within the aperture screen corresponded to the inocculation spacing within the plane of the biological plate. For example, it can be seen from FIG. 2 and FIG. 4 that the transparent circular discs 8 or the orifices 15 are in opposition to the object positions. To provide an indirect illumination of microbiological plates with surface objects, the plates are positioned at a relatively large particular spacing above the first aperture screen 4. The optimum spacing a can be experimentally determined in the following manner. If the light beam emitted from the diffusion discs 6 is followed up, which light beam is conditioned to traverse the orifices in the two aperture screens 4 and 5, it can thus be seen that there are several planes at the spacing $a_1$, $a_2$ above the aperture screen 4, which planes are crossed at almost every position by one of the diagonally incident light beams. When progressing along the intersection line of these planes, areas alternate, which are intercepted at the same angle by light beams running diagonally towards the left or diagonally towards the right. It is important that, from the reference point of the plates, the usual identical angles arise in the diagonal light illumination. The right-/left-alternation in the diagonal light illumination is, however, of no importance to the light scattering process within the bacterial growth areas.

The observation of parallel beams according to FIG. 7 is oversimplified. In reality, all light beams diverge substantially. This has a favourable effect to smooth out the light intensities arising on the planes $E_1$ and $E_2$. The position of the optimum plane (planes) in which fluctuations in light intensity are minimum, is best established experimentally, as already mentioned. For this purpose, a light diffusing disc is provided at a spacing a and ensures that minimum fluctuations of the diffused light intensity exist at this position.

As already explained above, there is no established connection, in the case of surface microbiological structures, between the aperture spacings within the aperture screen and the dimensions of the microbiological structure. Since even with the optimum spacing a between the plane of the object to be measured and the first aperture screen 4, a slight residual ripple of the illumination intensity cannot be avoided, it is favourable if the aperture spacing within the aperture screen is small in relation to the dimensions of the object structures expected. The dimensions of the object structures correspond in these cases to the diameter of the inhibiton zones or to the size of the colony.

All in all, it has become clear that the principle of the complementary aperture screens, apart from specific methodologic modifications, can be universally used for illuminating microbiological structures, which are fully automatically analysed regarding position (localization) and size (diameter determination) and optical properties (density, colour, inter alia) by a video camera. By the described measures, which are relatively low in cost regarding apparatus technology, the contrast of the microbiological structures in relation to the background is clearly increased in all cases. At the same time, there is an achievement in that the illumination intensity within the total object plane is almost constant and in that the overall physical height of the multilayered illumination structure remains small.

We claim:

1. An illuminating device for the optical, particularly image-analytical evaluation of a microbiological structure with a diffused radiating surface light source and an aperture system positioned between the microbiological structure and the light source wherein the aperture system comprises two optically complementary aperture screens (4,5) disposed in series; the first aperture screen(4) consists of a large number of transparent circular discs (8); positioned at intervals on an opaque base and the second aperture screen (5) consists of a large number of opaque circular discs (9); positioned at intervals on a transparent base; and wherein the opaque circular discs (9) are larger in diameter than the transparent circular discs (8); so that the circular disc of both aperture screens (4 and 5) overlap in a projection.

2. An illuminating device according to claim 1, wherein in order to examine a microbiological structure consisting of a large number of individual objects; the central points of the circular discs (8 and 9) of the two aperture screens (4 and 5) lie on the extension of the connecting straight lines from a vanishing point F on the optical axis to the object positions (2).

3. An illuminating device according to claim 1, wherein in order to examine a microbiological structure consisting of relatively large surface objects; the transparent circular discs (8) of the first aperture screen (4) are positioned substantially concentrically in a parallel projection to the opaque circular discs (9) of the second aperture screen (5).

4. An illuminating device according to claim 1, wherein a spacing h between the two aperture screens (4,5) is from 0.5 to 5 times larger than the diameter of the transparent circular discs (8) of the first aperture screen (4).

5. An illuminating device according to claim 1, wherein the difference in diameter of the circular discs of the two aperture screens (4,5) is from 5% to 100% of a spacing between the two aperture screens.

6. An illuminating device according to claim 1, wherein the aperture screens (4,5) consist of photographically produced masks base on commercial photographic material.

7. An illuminating device according to claim 1, wherein the first aperture screen (4) is part of a sample holding device (14) used for the microbiological structure.

8. An illuminating device according to claim 7, further comprising a further aperture screen (17) with one or more transparent circular discs (18) and positioned above the sample holding device (14) for cutting out stray light which is emitted from the sample holding device (14).

* * * * *